United States Patent [19]

Iori et al.

[11] 4,392,883
[45] Jul. 12, 1983

[54] HERBICIDAL COMPOSITION AND PROCESS

[75] Inventors: Shinichi Iori; Ikuo Kajiwara, both of Shizuoka; Kazuo Jikihara, Niiza, all of Japan

[73] Assignee: Kumiai Chemical Industry Co. Ltd., Tokyo, Japan

[21] Appl. No.: 237,093

[22] Filed: Feb. 23, 1981

[51] Int. Cl.³ .................... A01N 43/64; A01N 37/00
[52] U.S. Cl. ............................................ 71/93; 71/100
[58] Field of Search .................................... 71/93, 100

[56] References Cited

U.S. PATENT DOCUMENTS 3,849,109 11/1974 Kato et al. .......................... 71/100
4,028,091 6/1977 Jikihara et al. ...................... 71/93

FOREIGN PATENT DOCUMENTS 2413262 9/1975 Fed. Rep. of Germany .......... 71/93
2528302 1/1977 Fed. Rep. of Germany .......... 71/93
50-40745 4/1975 Japan ...................................... 71/93

Primary Examiner—Glennon H. Hollrah
Attorney, Agent, or Firm—Larson and Taylor

[57] ABSTRACT

A herbicidal composition is provided which is characterized by the combination use as active ingredients of a thiocarbamate derivative of formula I:

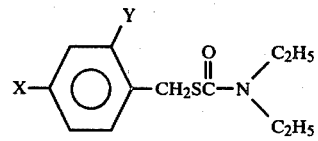

wherein one of X and Y is a hydrogen and the other is a chlorine and 4-amino-3-methyl-6-phenyl-1,2,4-triazin-5(4H)-one of the formula:

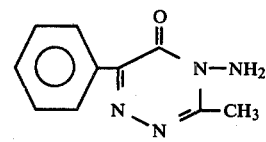

Also provided is a process of inhibiting the growth of unwanted plants by applying the herbicidal composition to the plants or to the soil where the plants are grown.

4 Claims, No Drawings

HERBICIDAL COMPOSITION AND PROCESS

TECHNICAL FIELD OF THE INVENTION

This invention relates to a herbicidal composition and, more particularly, to a herbicidal composition comprising a thiocarbamate derivative and a triazine derivative in combination as active ingredients, and to herbicidal processes using the composition.

BACKGROUND OF THE INVENTION

In recent years, many herbicides have been developed and put to practical applications, resulting in the saving of labor in agricultural works. However, since there occurred various problems on efficacy and safety of the herbicidal chemicals in the practical applications thereof, the arrival of further improved herbicides has earnestly been desired. Namely, the related art is strongly requiring highly safe herbicides which have no affection on useful crops, which effectively act against harmful weeds at a low application rate and which give no environmental pollution.

The object of this invention is to provide a herbicidal composition and process adaptable to such requirements.

BRIEF SUMMARY OF THE INVENTION

This invention provides as a first aspect a herbicidal composition comprising a thiocarbamate derivative of the general formula:

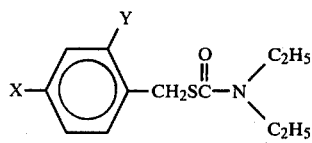

wherein one of X and Y is a hydrogen and the other is a chlorine and 4-amino-3-methyl-6-phenyl-1,2,4-triazin-5(4H)-one of the formula:

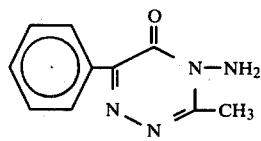

as active ingredients.

DETAILED DESCRIPTION OF THE INVENTION

The compounds of formula I to be used in the composition according to this invention are known as an effective herbicide for killing a variety of annual gramineous weeds such as *Echinochloa spp., Digitaria spp., Setaria spp.* and *Poa annua spp.* and annual *Cyperus spp.* and to be useful for weeding in such crops as rice, maize, soybean and beet plants.

The compound of formula II is also known as a herbicide for killing various annual broad-leaved weeds such as *Polygonum spp., Chenopodium album, Amaranthus albus* and *Stellaria media* by treatments during their growing period with such a high security that it does not substantially damage certain crop plants, notably beet.

However, each of the compounds of formulae I and II is not always effective as a completely selective herbicide if used in a small amount or at a low concentration for killing weeds growing in beet farms. Thus, the compounds of formula I have an excellent herbicidal activity against gramineous weeds by pre-emergence application without affecting beet crops, but are insufficient in a small amount or at a low concentration to completely kill broad-leaved weeds and gramineous weeds by post-emergence application. On the other hand, the compound of formula II exhibits an excellent herbicidal activity against broad-leaved weeds by post-emergence application with a high selectivity that it does not substantially affect beet crops, but is ineffective against broad-leaved weeds and gramineous weeds by pre-emergence application. The latter compound is also insufficient in its herbicidal activity when it rains early after application thereof or against old-aged broad-leaved weeds.

The combination of the two compounds of formulae I and II according to this invention makes it possible to kill pre-emergence broad-leaved weeds, post-emergence gramineous weeds and old-aged broad-leaved weeds, which were impossible by application of each single compound. Thus, the composition of this invention exhibits a significant herbicidal activity against a wide variety of unwanted weeds including annual gramineous weeds and broad-leaved weeds over the whole growing periods by pre- and post-emergence applications in a small amount or at a low concentration. Further, the composition of this invention is resistant to rain after the application, thus lasting a stable herbicidal activity. The high stability under various conditions, the high activity particularly against old-aged broad-leaved weeds and the immediate effect of the composition according to this invention are presumed to be due to the ease of the compound of formula II to be absorbed into the body of weeds by the aid of the compound of formula I.

In fact, this invention is based on the discovery that the combination of the compounds of formulae I and II not only supplies the deficiencies of the application of each single compound as above-mentioned, but also provides an unexpectedly high synergistic effect in such a manner that the composition of this invention can kill both the gramineous weeds and broad-leaved weeds growing in beet farms simultaneously and exhibit a high herbicidal activity over the whole growing periods of weeds by pre- and post-emergence applications. It has also been found that the composition of this invention is effectively applicable not only to the weeding of beet farms, but also to that of spinach, barley, wheat and maize farms.

In a further aspect, therefore, the invention provides a process of inhibiting the growth of weeds in crops of beet, spinach, barley, wheat and maize which comprises applying to the crop area, before or after the crop emerges, a composition comprising a compound of formula I and a compound of formula II as active ingredients in an amount sufficient to inhibit the growth of the weeds but insufficient substantially to damage the crop plants. In the pre-emergence application, the composition may be applied to soils in which seeds of the crop plants have been sown, preferably by spraying. In the post-emergence application, the composition is usually applied to stalks and leaves of plants, preferably by spraying.

Examples of the compounds of formula I used in the composition of this invention are as follows:

Compound A

S-(p-chlorobenzyl)-N,N-diethylthiocarbamate

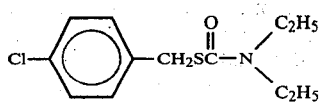

Compound B

S-(o-chlorobenzyl)-N,N-diethylthiocarbamate

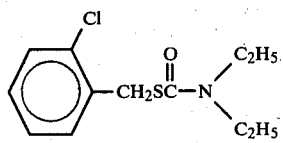

The synergistic effect of the herbicidal composition of this invention is particularly significant at certain specific ratios of the compound of formula I and the compound of formula II, but the ratio of the two compounds to be incorporated may vary over a relatively wide range. In general, it is desirable to use 0.05 to 10 parts by weight, more preferably 0.125 to 4 parts by weight, and most preferably 0.25 to 2 parts by weight, of the compound of formula II (hereinafter referred to as Compound C) per part by weight of the compound of formula I.

The herbicidal composition of this invention may be prepared in any form of preparations containing typically 0.5 to 80% by weight of the active ingredients, such as wettable powders or grains, emulsions, powders, grains, granules, flowable suspensions and the like.

In preparing the herbicidal composition of this invention, the active ingredients are mixed with a diluent or carrier. Suitable solid diluents or carriers include, for example, talc, bentonite, clay, kaolin, diatomaceous earth, white carbon, vermiculite, slaked lime, siliceous sand, calcium carbonate, dolomite, powdered magnesia, Fuller's earth, ammonium sulfate and urea. Suitable liquid diluents or carriers include, for example, alcohols, dioxane, acetone, cyclohexane, methylnaphthalene, dimethylformamide and acetonitrile.

Surface active agents which may be used as emulsifying, dispersing or suspending agent in the composition of this invention may be of the cationic, anionic or non-ionic type. Suitable agents of the cationic type include, for example, quaternary ammonium compounds such as cetyltrimethyl ammonium bromide. Suitable agents of the anionic type include, for example, soaps, salts of aliphatic mono-esters of sulphuric acid such as sodium lauryl sulfate, and salts of sulfonated aromatic compounds such as dodecylbenzene-sulfonate, sodium, calcium or ammonium lignosulfonate and butylnaphthalene sulfonate. Suitable agents of the non-ionic type include, for example, the condensation products of ethylene oxide with fatty alcohols such as oleyl alcohol and cetyl alcohol, or with alkyl phenols such as octylphenol, nonylphenol and octylcresol, the partial esters derived from long chain fatty acids and hexitol anhydrides such as sorbitol monolaurate and the condensation products of the said partial esters with ethylene oxide such as polyoxyethylene sorbitan monolaurate. Various other additives which are conventionally used in formulating herbicidal compositions such as carboxymethylcellulose and acasia gum may also be used.

The dose of the active ingredients of the composition of this invention depends upon weather condition, soil condition, form of the composition, season of the application, method of the application, kind of crop plants, kind of weeds and growth stage of weeds and it is usually in a range of 0.5 to 30 kg, preferably 2 to 12 kg and especially 5 to 8 kg per hectare in the soil treatment or the foliage treatment. The composition is usually applied in a concentration of 500 to 30,000 ppm, preferably 2,000 to 20,000 ppm and especially 5,000 to 10,000 ppm of the active ingredients. In the case of application of the herbicidal composition spraying from an airplane, the concentration of the active ingredients is usually in a range of 10,000 to 75,000 ppm. For example, 0.5 to 1.5 kg of the active ingredients is sprayed at a rate of 20 to 50 liter/ha.

Upon applications, the herbicidal composition of this invention in the form undiluted or diluted with water is applied to soils or stalks and leaves of plants as abovementioned. It is also possible to add other herbicidal chemical(s) to the herbicidal composition of this invention to substantially enhance the herbicidal activity thereof.

PREFERRED EMBODIMENTS OF THE INVENTION

The present invention will be further explained more specifically by reference to the following formulation embodiments and examples but the invention is not to be construed as being limited thereto. Thus, proportions of respective ingredients incorporated and kinds of carriers used can be varied as desired. Unless otherwise indicated, all parts, percents, ratios and the like are by weight.

(a) Emulsifiable concentrate:

5–80 Percent, preferably 10–70% and most preferably 15–30%, of the active ingredients, wherein the ratio of the compounds of formulae I and II is 1:0.05–10, is dissolved in 5–90%, preferably 30–60%, of a liquid carrier, to which is added 1–40%, preferably 5–20%, of an emulsifying agent.

(b) Wettable powder:

5–80 Percent, preferably 20–50%, of the active ingredients, wherein the ratio of the compounds of formulae I and II is 1:0.05–10, 1–20%, preferably 5–10%, of a surface active agent and 5–85%, preferably 40–70% of a solid carrier are crushed and mixed well.

(c) Dust:

0.5–10 Percent, preferably 1–5%, of the active ingredients, wherein the ratio of the compounds of formulae I and II is 1:0.05–10, is crushed and mixed well with 90–99.5%, preferably 95–99%, of a solid carrier.

(d) Granules:

0.5–40 Percent, preferably 2–10%, of the active ingredients, wherein the ratio of the compounds of formulae I and II is 1:0.05–10, is crushed and mixed well with 60–99.5%, preferably 90–98%, of a solid carrier and the mixture is kneaded with the addition of water, granulated and dried to yield granules.

EXAMPLE 1

Wettable powder

A wettable powder is prepared by homogeneously mixing and grinding 30 parts of Compound A, 20 parts of Compound C, 2 parts of sodium alkylbenzenesulfonate, 3 parts of polyvinylalcohol, 20 parts of white carbon and 25 parts of fine powdered clay.

EXAMPLE 2

Wettable powder

A wettable powder is prepared by homogeneously mixing and grinding 40 parts of Compound B, 20 parts of Compound C, 2 parts of sodium alkylbenzenesulfonate, 3 parts of polyvinylalcohol, 20 parts of white carbon and 15 parts of diatomaceous earth.

EXAMPLE 3

Wettable powder

A wettable powder is prepared by homogeneously mixing and grinding 30 parts of Compound A, 10 parts of Compound C, 2 parts of sodium alkylbenzenesulfonate, 3 parts of polyvinylalcohol, 20 parts of white carbon and 35 parts of fine powdered clay.

EXAMPLE 4

Wettable powder

A wettable powder is prepared by homogeneously mixing and grinding 40 parts of Compound B, 10 parts of Compound C, 2 parts of sodium alkylbenzenesulfonate, 3 parts of polyvinylalcohol, 20 parts of white carbon and 25 parts of fine powdered clay.

EXAMPLE 5

Wettable powder

A wettable powder is prepared by homogeneously mixing and grinding 30 parts of Compound A, 30 parts of Compound C, 2 parts of sodium alkylbenzenesulfonate, 3 parts of polyvinylalcohol, 20 parts of white carbon and 15 parts of diatomaceous earth.

EXAMPLE 6

Wettable powder

A wettable powder is prepared by homogeneously mixing and grinding 50 parts of Compound A, 2.5 parts of Compound C, 3 parts of polyoxyethylenealkylarylether, 3 parts of calcium lignosulfonate, 30 parts of white carbon and 11.5 parts of fine powdered clay.

EXAMPLE 7

Wettable powder

A wettable powder is prepared by homogeneously mixing and grinding 5 parts of Compound B, 50 parts of Compound C, 2 parts of sodium alkylbenzenesulfonate, 3 parts of calcium lignosulfonate, 10 parts of diatomaceous earth and 30 parts of fine powdered clay.

EXAMPLE 8

Emulsion

An emulsion is prepared by homogeneously mixing 10 parts of Compound A, 20 parts of Compound C, 6 parts of polyoxyethylenealkylarylether, 4 parts of sodium alkylarylsulfonate and 60 parts of dimethylformamide.

EXAMPLE 9

Emulsion

An emulsion is prepared by homogeneously mixing 30 parts of Compound B, 5 parts of Compound C, 4 parts of sodium alkylarylsulfonate, 6 parts of polyoxyethylenealkylarylether and 55 parts of dimethyl sulfoxide.

EXAMPLE 10

Granules

A composition in the form of granules is prepared by homogeneously mixing and grinding 5 parts of Compound A, 5 parts of Compound C, 2 parts of polyvinylalcohol, 15 parts of diatomaceous earth and 73 parts of clay, kneading the ground mixture with the addition of water, granulating the mixture and drying the resulting granules.

EXAMPLE 11

Granules

A composition in the form of granules is prepared by dissolving 10 parts of Compound A and 0.5 parts of Compound C in 3 parts of dimethylformamide and spraying 86.5 parts of diatomaceous earth in the form of granules with the resulting solution.

EXAMPLE 12

Granules

A composition in the form of granules is prepared by homogeneously mixing and grinding 1 part of Compound B, 10 parts of Compound C, 1 part of sodium alkylbenzene sulfonate, 5 parts of white carbon, 50 parts of bentonite and 30 parts of talc, kneading the ground mixture, granulating the mixture and drying the resulting granules.

EXAMPLE 13

Powder

A powder composition is prepared by homogeneously mixing and grinding 3 parts of Compound B, 1 part of Compound C, 0.5 parts of white carbon and 95.5 parts of clay.

EXAMPLE 14

Powder

A powder composition is prepared by homogeneously mixing and grinding 8 parts of Compound A, 0.5 parts of Compound C, 15 parts of diatomaceous earth, 50 parts of clay and 26.5 parts of talc.

EXAMPLE 15

Powder

A powder composition is prepared by homogeneously mixing and grinding 0.5 parts of Compound B, 5 parts of Compound C, 2 parts of white carbon and 94.5 parts of clay.

The following Examples (tests) were performed to demonstrate the excellent herbicidal activity of the composition of this invention. In each test, it is suggested that the use of each single compound gives insufficient herbicidal activity, but the combined use of those compounds according to this invention exhibits a higher herbicidal activity than the simple sum of the activities of respective compounds over a wide range of weeds.

EXAMPLE 16

This Example illustrates the herbicidal activities on a variety of unwanted weeds and the phytotoxicity to beet of compositions according to this invention by pre-emergence treatment. Thirty (30) seeds each of beet (*Beta vulgaris*), barnyard grass (*Echinochloa crusgalli*), annual bluegrass (*Poa annua*), smartweed (*Polygonum lapathifolium*) and goosefoot (*Chenopodium album var. centrorubrum Makino*) were sown in farm-soil contained in each of 2,000 cm² polyethylene containers. After covering the seeds with the soil, each of the wettable powders prepared in Examples 1 and 3 in the form diluted with water to give the concentrations of active compounds shown in Table 1 was uniformly sprayed on to the soil at an application rate equivalent to 500 liters per hectare. After the lapse of 25 days from the spraying, the fresh weight of the plants tested was measured, from which the growth inhibition (%) was calculated as follows:

$$\text{Growth inhibition (\%)} = \left(1 - \frac{\text{Fresh weight of the plant grown in the treated plot}}{\text{Fresh weight of the plant grown in the untreated plot}}\right) \times 100 \qquad \text{III}$$

The results obtained are shown in Table 1. By way of comparison, similar tests were conducted wherein each compound used in the composition above was used separately under the same conditions as above and the results are also shown in Table 1.

TABLE 1

Herbicidal activity and phytotoxicity to beet by pre-emergence treatment

| Compound | Application rate (kg/ha) | Beet | Barnyard grass | Annual bluegrass | Smartweed | Goosefoot |
|---|---|---|---|---|---|---|
| A | 3 | 0 | 89 | 86 | 23 | 19 |
| B | 3 | 0 | 81 | 83 | 25 | 20 |
| C | 2 | 0 | 23 | 63 | 100 | 100 |
|   | 1 | 0 | 6 | 20 | 80 | 79 |
| A+C | 3, 2 | 0 | 100 | 100 | 100 | 100 |
| A+C | 3, 1 | 0 | 100 | 100 | 100 | 100 |
| B+C | 3, 2 | 0 | 100 | 100 | 100 | 100 |
| B+C | 3, 1 | 0 | 100 | 100 | 100 | 100 |

EXAMPLE 17

This Example illustrates the herbicidal activities on various unwanted weeds and the phytotoxicity to beet of compositions according to this invention by post-emergence treatment. In each of 2,000 cm² polyethylene containers filled with a farm-soil, beet (1.5 to 2 leaved stage), barnyard grass (2 to 2.5 leaved stage), annual bluegrass (1.5 to 2 leaved stage), smartweed (1 to 2 leaved stage) and goosefoot (1.5 to 2 leaved stage) were grown to such degrees as shown in the above brackets, respectively. Each of the wettable powders prepared in Examples 2 and 4 was diluted with water to give the concentrations of active compounds shown in Table 2 and sprayed onto the stalks and leaves of the growing plants at an application rate of 500 liters per hectare. Twenty days after the spraying, the fresh weight of the plants tested was measured, from which the growth inhibition (%) was calculated according to formula III. The results are as shown in Table 2.

TABLE 2

Herbicidal activity and phytotoxicity to beet by treatment on stalks and leaves in growing stage

| Compound | Application rate (kg/ha) | Beet | Barnyard grass | Annual bluegrass | Smartweed | Goosefoot |
|---|---|---|---|---|---|---|
| A | 4 | 0 | 78 | 70 | 13 | 10 |
| B | 4 | 0 | 75 | 70 | 16 | 14 |
| C | 2 | 0 | 8 | 14 | 56 | 59 |
|   | 1 | 0 | 4 | 9 | 32 | 40 |
| A+C | 4, 2 | 0 | 100 | 100 | 98 | 100 |
| A+C | 4, 1 | 0 | 96 | 100 | 86 | 93 |
| B+C | 4, 2 | 0 | 100 | 100 | 100 | 100 |
| B+C | 4, 1 | 0 | 95 | 100 | 85 | 96 |

EXAMPLE 18

This Example illustrates the herbicidal activities on yellow fox tail (*Setaria viridis Beauv.*) and amaranth (*Amaranthus albus*) of compositions according to this invention by pre-emergence and post-emergence treatments. Seeds of the test species were placed on the surface of 2,000 cm² polyethylene containers of soil and covered with 0.5 cm thickness of the soil. Each of the wettable powders prepared in Examples 5 and 4 was diluted with water to give the concentration of active compounds shown in Table 3 and sprayed onto the soil in the pre-emergence tests and onto the stalks and leaves of the growing plants in the post-emergence tests at an application rate of 500 liters per hectare. Twenty days after the spraying, the fresh weight of the plant tested was measured, from which the growth inhibition (%) was calculated according to formula III. The results are shown in Table 3.

TABLE 3

Herbicidal activity by treatment in different growth stages

| Compound | Application rate (kg/ha) | S.v. Pre-emergence | A.a. Pre-emergence | S.v. 0.5 ~ 1 L | A.a. 1 ~ 1.5 L | S.v. 1.5 ~ 2 L | A.a. 2.5 ~ 3 L | S.v. 2.5 ~ 3 L | A.a. 3.5 ~ 4.5 L |
|---|---|---|---|---|---|---|---|---|---|
| A | 4 | 98 | 53 | 86 | 50 | 42 | 11 | 10 | 0 |
| B | 4 | 100 | 58 | 88 | 52 | 47 | 20 | 13 | 7 |
| C | 4 | 4 | 0 | 0 | 92 | 0 | 79 | 0 | 42 |
|   | 1 | 9 | 0 | 0 | 88 | 0 | 51 | 0 | 14 |
| A+ | 4 | 100 | 100 | 100 | 100 | 93 | 97 | 60 | 89 |

TABLE 3-continued

| Compound | Application rate (kg/ha) | Herbicidal activity by treatment in different growth stages | | | | | | | |
|---|---|---|---|---|---|---|---|---|---|
| | | S.v. Pre-emergence | A.a. 0.5 ~ 1 L | S.v. 1 ~ 1.5 L | A.a. 1.5 ~ 2 L | S.v. 1.5 ~ 2 L | A.a. 2.5 ~ 3 L | S.v. 2.5 ~ 3 L | A.a. 3.5 ~ 4.5 L |
| C | 4 | | | | | | | | |
| A 4 + C 1 | | 100 | 96 | 100 | 100 | 89 | 92 | 58 | 84 |
| B 4 + C 4 | | 100 | 100 | 100 | 100 | 96 | 99 | 66 | 92 |
| B 4 + C 1 | | 100 | 100 | 98 | 100 | 92 | 96 | 60 | 91 |
| Untreated | — | 0 | 0 | 0 | 0 | 0 | 0 | 0 | 0 |

S.v.: *Setaria viridis Beauv.*;
A.a.: *Amaranthus albus*
0.5 ~ 1 L: 0.5 ~ 1 leaved stage

What we claim is:

1. A herbicidal composition for inhibiting growth of smartweed, goosefoot and barnyardgrass consisting essentially of an effective amount of a mixture of a thiocarbamate derivative of the general formula:

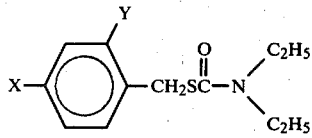

wherein one of X and Y represents a hydrogen atom and the other is a chlorine atom, and 4-amino-3-methyl-6-phenyl-1,2,4-triazin-5(4H)-one of the formula:

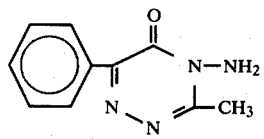

in a ratio of 1:1 to 4:1 by weight as active ingredients.

2. A herbicidal composition as claimed in claim 1 wherein the ratio of the compound of formula I and the compound of formula II is 2:1 by weight.

3. A process of inhibiting the growth of smartweed, goosefoot and barnyard grass which comprises applying to the plants or to the soil where the plants are grown 5–8 kg per hectare of a composition consisting essentially of a mixture of a thiocarbamate derivative of the general formula:

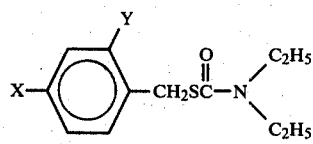

wherein one of X and Y represents a hydrogen atom and the other is a chlorine atom, and 4-amino-3-methyl-6-phenyl-1,2,4-triazin-4(4H)-one of the formula:

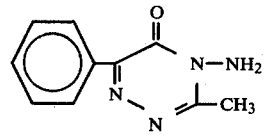

in a ratio of 1:1 to 4:1 by weight as active ingredients.

4. A process as claimed in claim 3 wherein the ratio of the compound of formula I and the compound of formula II is 2:1.

* * * * *